(12) United States Patent
Giron et al.

(10) Patent No.: US 10,265,260 B2
(45) Date of Patent: Apr. 23, 2019

(54) TRANSFER MAKEUP PROCESS AND RELATED DEVICE

(71) Applicant: L'OREAL, Paris (FR)

(72) Inventors: Franck Giron, Lagny sur Marne (FR); Henri Samain, Bievres (FR)

(73) Assignee: L'OREAL, Paris (FR)

( * ) Notice: Subject to any disclaimer, the term of this patent is extended or adjusted under 35 U.S.C. 154(b) by 0 days.

(21) Appl. No.: 15/108,303

(22) PCT Filed: Nov. 19, 2014

(86) PCT No.: PCT/IB2014/067136
§ 371 (c)(1),
(2) Date: Jun. 26, 2016

(87) PCT Pub. No.: WO2015/097618
PCT Pub. Date: Jul. 2, 2015

(65) Prior Publication Data
US 2016/0317417 A1    Nov. 3, 2016

(30) Foreign Application Priority Data

Dec. 27, 2013 (FR) ...................................... 13 63638

(51) Int. Cl.
*B41J 3/407* (2006.01)
*A61K 8/60* (2006.01)
(Continued)

(52) U.S. Cl.
CPC .............. *A61K 8/602* (2013.01); *A45D 40/30* (2013.01); *A61K 8/345* (2013.01); *A61K 8/466* (2013.01);
(Continued)

(58) Field of Classification Search
CPC .............. B41M 5/0041; B41M 5/0047; B41M 5/0082; B41M 5/0088; B41M 5/025;
(Continued)

(56) References Cited

U.S. PATENT DOCUMENTS

| 4,137,180 A | 1/1979 | Naik et al. |
| 4,804,719 A | 2/1989 | Weaver et al. |

(Continued)

FOREIGN PATENT DOCUMENTS

| CN | 1476319 A | 2/2004 |
| CN | 1519278 A | 8/2004 |

(Continued)

OTHER PUBLICATIONS

Computer-generated translation of JP 2007-204487, published on Aug. 2007.*

(Continued)

*Primary Examiner* — Huan Tran
(74) *Attorney, Agent, or Firm* — Shumaker, Loop & Kendrick, LLP (57) ABSTRACT

The present invention relates to a printer containing at least one cosmetic ink and designed to allow the formation of a coat of cosmetic ink on a non-flat transfer surface defined by a substrate and intended to transfer the coat of ink by contact onto human keratin materials.

17 Claims, 2 Drawing Sheets

(51) Int. Cl.

| | |
|---|---|
| *B41J 2/005* | (2006.01) |
| *A45D 40/30* | (2006.01) |
| *A61K 8/34* | (2006.01) |
| *A61K 8/46* | (2006.01) |
| *A61K 8/49* | (2006.01) |
| *A61Q 19/04* | (2006.01) |
| *C09D 11/328* | (2014.01) |
| *C09D 11/40* | (2014.01) |
| *B41J 2/01* | (2006.01) |

(52) U.S. Cl.
CPC .......... *A61K 8/4913* (2013.01); *A61K 8/4946* (2013.01); *A61Q 19/04* (2013.01); *B41J 2/0057* (2013.01); *B41J 2/01* (2013.01); *B41J 3/407* (2013.01); *C09D 11/328* (2013.01); *C09D 11/40* (2013.01); *A61K 2800/43* (2013.01); *A61K 2800/87* (2013.01); *B41J 2002/012* (2013.01)

(58) Field of Classification Search
CPC .. B41M 5/0256; B41M 5/035; B41M 5/0076; A45D 2200/1009; A45D 2200/1018; A45D 2200/1036; A45D 2200/25; A45D 40/30; A45D 40/26; B41J 2/0057; B41J 3/407; B41J 2/01; B41J 2/325; B41J 3/4073; B41J 2002/012; B41J 2/32; A61Q 1/025
See application file for complete search history.

(56) References Cited

U.S. PATENT DOCUMENTS

| | | | |
|---|---|---|---|
| 4,874,554 A | 10/1989 | Lange et al. | |
| 4,925,667 A | 5/1990 | Fellows et al. | |
| 4,999,418 A | 3/1991 | Krutak et al. | |
| 5,030,708 A | 7/1991 | Krutak et al. | |
| 5,032,670 A | 7/1991 | Parham et al. | |
| 5,043,376 A | 8/1991 | Sharma et al. | |
| 5,047,084 A | 9/1991 | You et al. | |
| 5,078,160 A * | 1/1992 | Carbonnier | A45D 40/00 132/320 |
| 5,102,980 A | 4/1992 | Krutak et al. | |
| 5,104,913 A | 4/1992 | Sharma et al. | |
| 5,106,942 A | 4/1992 | Krutak et al. | |
| 5,194,463 A | 3/1993 | Krutak et al. | |
| 5,281,659 A | 1/1994 | Weaver et al. | |
| 5,958,560 A | 9/1999 | Ewan | |
| 5,997,134 A | 12/1999 | Hotomi et al. | |
| 5,997,136 A | 12/1999 | Fujisawa et al. | |
| 6,013,248 A | 1/2000 | Luebbe et al. | |
| 6,106,852 A | 8/2000 | Vineberg | |
| 6,168,656 B1 | 1/2001 | Schulz et al. | |
| 6,190,730 B1 | 2/2001 | Matsos et al. | |
| 6,299,967 B1 | 10/2001 | Collins et al. | |
| 6,312,124 B1 * | 11/2001 | Desormeaux | B41J 2/16505 347/109 |
| 6,342,094 B1 | 1/2002 | Kabalnov | |
| 6,367,484 B1 | 4/2002 | Ramin et al. | |
| 6,428,164 B1 | 8/2002 | Missell et al. | |
| 6,543,893 B2 * | 4/2003 | Desormeaux | B41J 2/16505 347/109 |
| 6,622,733 B2 * | 9/2003 | Saksa | A45D 34/04 132/200 |
| 6,626,183 B1 | 9/2003 | Pietrocola | |
| 7,241,503 B2 | 7/2007 | Noguchi | |
| 8,007,062 B2 | 8/2011 | Edgar et al. | |
| 8,083,422 B1 * | 12/2011 | Simmons | B41J 3/36 347/109 |
| 8,545,613 B2 * | 10/2013 | Blette | A61K 8/345 106/31.03 |
| 8,695,610 B2 * | 4/2014 | Samain | A45D 44/005 132/200 |
| 8,919,247 B2 * | 12/2014 | Morgavi | B41J 2/0057 101/38.1 |
| 9,616,668 B1 * | 4/2017 | Rabe | B41J 3/36 |
| 2002/0110672 A1 | 8/2002 | Muratore-Pallatino et al. | |
| 2002/0155069 A1 * | 10/2002 | Pruche | A61K 9/0075 424/46 |
| 2002/0164295 A1 | 11/2002 | Scavone et al. | |
| 2004/0057742 A1 | 3/2004 | Richtsmeier | |
| 2004/0078278 A1 * | 4/2004 | Dauga | A45D 44/005 434/100 |
| 2005/0148908 A1 * | 7/2005 | Skover | A61Q 19/08 601/17 |
| 2006/0093943 A1 | 5/2006 | Shu et al. | |
| 2006/0098076 A1 * | 5/2006 | Liang | A45D 44/005 347/129 |
| 2007/0144634 A1 | 6/2007 | Hitchcock | |
| 2008/0053476 A1 | 3/2008 | LaHood et al. | |
| 2008/0176160 A1 | 7/2008 | Deprez et al. | |
| 2009/0325221 A1 | 12/2009 | Long et al. | |
| 2010/0031834 A1 | 2/2010 | Morgavi et al. | |
| 2010/0086693 A1 | 4/2010 | Yamada et al. | |
| 2011/0020023 A1 | 1/2011 | Hirai | |
| 2011/0025040 A1 | 2/2011 | Dominguez | |
| 2011/0141188 A1 | 6/2011 | Morita | |
| 2011/0159463 A1 * | 6/2011 | Samain | A45D 44/005 434/100 |
| 2011/0164263 A1 | 7/2011 | Samain et al. | |
| 2011/0268873 A1 | 11/2011 | Blette | |
| 2012/0027423 A1 | 2/2012 | Kawai | |
| 2012/0244316 A1 | 9/2012 | Dobler et al. | |
| 2012/0244465 A1 | 9/2012 | Kobayashi | |
| 2012/0307304 A1 | 12/2012 | Moreno | |
| 2013/0216295 A1 | 8/2013 | Wong | |
| 2014/0233967 A1 | 8/2014 | Suzuki | |
| 2014/0345639 A1 * | 11/2014 | Samain | A61Q 1/02 132/200 |
| 2015/0053759 A1 | 2/2015 | Cahill et al. | |
| 2015/0150767 A1 | 6/2015 | Klug et al. | |
| 2016/0103962 A1 | 4/2016 | Costantino et al. | |
| 2016/0316890 A1 * | 11/2016 | Samain | A61Q 1/025 |
| 2016/0316891 A1 * | 11/2016 | Samain | B44C 1/1733 |
| 2016/0316892 A1 * | 11/2016 | Giron | B41M 5/0256 |
| 2016/0317403 A1 * | 11/2016 | Giron | A61K 8/466 |
| 2016/0324298 A1 * | 11/2016 | Samain | A61Q 1/02 |
| 2016/0324299 A1 * | 11/2016 | Samain | A61K 8/345 |

FOREIGN PATENT DOCUMENTS

| | | | |
|---|---|---|---|
| CN | 101010064 A | 8/2007 | |
| CN | 101056605 A | 10/2007 | |
| CN | 101980894 A | 2/2011 | |
| CN | 102490540 A | 6/2012 | |
| EP | 705593 A1 | 4/1996 | |
| EP | 0728460 A1 | 8/1996 | |
| EP | 0749746 A1 | 12/1996 | |
| EP | 0749747 A1 | 12/1996 | |
| EP | 780114 A1 | 6/1997 | |
| EP | 0923928 A1 | 6/1999 | |
| EP | 0930060 A1 | 7/1999 | |
| EP | 0938887 A1 | 9/1999 | |
| EP | 1000607 A1 | 5/2000 | |
| EP | 1048282 A1 | 11/2000 | |
| EP | 1059047 A1 | 12/2000 | |
| EP | 1304056 A2 | 4/2003 | |
| EP | 1925278 A1 | 5/2008 | |
| EP | 2090935 A1 | 8/2009 | |
| EP | 3211566 * | 8/2017 | .......... A45D 44/002 |
| FR | 2232303 A1 | 1/1975 | |
| FR | 2792192 A1 | 10/2000 | |
| FR | 2858226 A1 | 2/2005 | |
| FR | 2900594 * | 11/2007 | ........... B41M 5/025 |
| FR | 2905630 * | 3/2008 | ........... B41J 3/4073 |
| FR | 2905630 A1 | 3/2008 | |
| FR | 2909844 A1 | 6/2008 | |
| FR | 2939033 A1 | 6/2010 | |
| JP | S63-188616 A | 8/1988 | |
| JP | H04-208997 A | 7/1992 | |
| JP | H11-007203 A | 1/1999 | |

(56) References Cited

FOREIGN PATENT DOCUMENTS

| | | | | |
|---|---|---|---|---|
| JP | H11169231 A | 6/1999 | | |
| JP | 2001-245945 A | 9/2001 | | |
| JP | 2001278739 A | 10/2001 | | |
| JP | 3266197 B2 | 1/2002 | | |
| JP | 2002-058528 A | 2/2002 | | |
| JP | 2002-148998 A | 5/2002 | | |
| JP | 2003006452 A | 1/2003 | | |
| JP | 2005040356 A | 2/2005 | | |
| JP | 2005-088434 A | 4/2005 | | |
| JP | 2007204487 | * | 8/2007 | ............... A61Q 1/00 |
| JP | 2007204487 A | 8/2007 | | |
| JP | 2008-127388 A | 6/2008 | | |
| JP | 2010-186133 A | 8/2010 | | |
| JP | 2012-002869 A | 1/2012 | | |
| JP | 2012-518457 A | 8/2012 | | |
| JP | 2012-520837 A | 9/2012 | | |
| JP | 2012249849 A | 12/2012 | | |
| JP | 2013-031504 A | 2/2013 | | |
| JP | 2013137758 A | 7/2013 | | |
| JP | 2013252709 | * | 12/2013 | ............... B41F 17/08 |
| WO | 1992007913 A1 | 5/1992 | | |
| WO | 9848659 A1 | 11/1998 | | |
| WO | 02/36083 A1 | 5/2002 | | |
| WO | 03033270 A1 | 4/2003 | | |
| WO | 2006/128737 A1 | 12/2006 | | |
| WO | 2006128737 A1 | 12/2006 | | |
| WO | 2007/134171 A1 | 11/2007 | | |
| WO | 2010/004526 A1 | 1/2010 | | |
| WO | 2010004526 A1 | 1/2010 | | |
| WO | 2010004531 A1 | 1/2010 | | |
| WO | 2010/095118 A | 8/2010 | | |
| WO | 2010/105842 A2 | 9/2010 | | |
| WO | 2012081065 A1 | 6/2012 | | |
| WO | 2013093889 A2 | 6/2013 | | |
| WO | 2013126513 A1 | 8/2013 | | |
| WO | 2013178701 A2 | 12/2013 | | |

OTHER PUBLICATIONS

Non-Final Office Action in U.S. Appl. No. 15/108,192 dated Oct. 6, 2017 (6 pages).
Restriction and Election of Species Requirement in U.S. Appl. No. 15/108,292 dated Mar. 1, 2017 (8 pages).
Non-Final Office Action in U.S. Appl. No. 15/108,076 dated Mar. 16, 2017 (12 pages).
"Papilio Laser Printable Temporary Tattoo Paper" (http://www.papilio.com/laser temporary tattoo paper.html), Dec. 14, 2013 (3 pages).
"Cheap laser printer paper for toner transfer?" (http://www.fountainpennetwork.com/forum/topic/41250-cheap-laser-printer-paper-for-toner-transfer/), Oct. 2, 2007 (11 pages).
First Office Action for CN Pat. Appln. No. 201480076509.2 with English Translation dated Oct. 30, 2017, 9 pages.
Final Rejection for U.S. Appl. No. 15/108,292 dated Jan. 30, 2018, 21 pages.
Non-Final Office Action for U.S. Appl. No. 15/108,292 dated Jul. 7, 2017.
International Search Report for PCT/IB2014/067130 dated Mar. 11, 2015 (5 pages).
International Search Report for PCT/IB2014/067132 dated Apr. 28, 2015 (4 pages).
International Search Report for PCT/IB2014/067133 dated Mar. 11, 2015 (5 pages).
International Search Report for PCT/IB2014/067134 dated Apr. 24, 2015 (4 pages).
International Search Report for PCT/IB2014/067136 dated Jul. 7, 2015 (5 pages).
International Search Report for PCT/IB2014/067138 dated Mar. 11, 2015 (3 pages).
Written Opinion for PCT/IB2014/067136 (7 pages).
Dyno Pretty Pup: "Dyno Pretty Pup Beauty Diary: LA Colors 30 Eye Design Palettes—Review." Mar. 16, 2012 (4 pages).
Office Action dated Sep. 10, 2018 in Japanese Patent Application No. 2016-542897 (7 pages).
Office Action dated Sep. 27, 2018 in U.S. Appl. No. 15/108,292 (16 pages).
pubchem; castor oil—https://pubchem.ncbi.nlm.nih.gov/compound/castor_oil#section=Top; 1 page; 2010.
Office Action dated Jul. 2, 2018 issued in Japanese Patent Application No. 2016-543073 (17pp).
Office Action dated Jun. 5, 2018 issued in Chinese Patent Application No. 201480074439.7 (16 pp).
Office Action dated Apr. 23, 2018 in European Patent Application No. 14 833 256.2.
Office Action dated May 18, 2018 for Chinese Patent Application No. 2014800713416 (22 pages).
Office Action issued in Chinese Application No. 201480071272.9 dated Jul. 2, 2018 (14 pp).
Office Action issued in U.S. Appl. No. 15/108,295 dated Aug. 6, 2018 (56 pp).
Office Action issued in U.S. Appl. No. 15/108,151 dated Aug. 7, 2018 (60 pp).
Final Rejection for U.S. Appl. No. 15/108,076 dated Aug. 21, 2017.
Canon, fix your own printer, https://www.fixyourownprinter.com/posts/66407 (dated: Mar. 17, 2010) (1 page).
Chinese Office Action dated Dec. 5, 2018 in Chinese Application No. 201480071307.9 (8 pages).
Japanese Office Action dated Nov. 19, 2018 for Japanese Application No. 2016-542996 (32 pages).
LA Colors 30 Eye Design Palettes—Review, Dyno Pretty Pup, http://dynopupbeauty.blogspot.nl/2012/03/la-colors-30-eye-design-palettes-review.html, Mar. 16, 2012 (5 pages).
Office Action for JP App. No. 2016-543027 dated Dec. 21, 2018 with English Translation (13 pages).
Office Action for JP App. No. 2016-543057 dated Dec. 17, 2018 with English Translation (14 pages).
Office Action for JP App. No. 2016-543072 dated Dec. 17, 2018 with English Translation(7 pages).
Office Action for JP App. No. 2016-543056 dated Dec. 17, 2018 with English Translation (7 pages).
Non-Final Office Action for U.S. Appl. No. 15/108,294 dated Mar. 4, 2019 (11 pgs.).
Non-Final Office Action for U.S. Appl. No. 15/108,302 dated Feb. 8, 2019 (7 pages).
Final Rejection for U.S. Appl. No. 15/108,295 dated Feb. 5, 2019 (10 pages).
Restriction Requirement for U.S. Appl. No. 15/108,305 dated Jan. 31, 2019 (8 pages).
English Translation of JP Office ACtion for JP Pat. App. No. 2016-542995 dated Jan. 16, 2019 and dated Jan. 21, 2019 (3 pages).

* cited by examiner

TRANSFER MAKEUP PROCESS AND RELATED DEVICE

BACKGROUND

It is difficult to make up keratin materials by transferring a deposit of ink printed on a substrate. The reason for this is that the known inks are such that, once the printing has been performed, they dry so quickly that transfer does not take place.

Moreover, it is desirable for the makeup device to provide satisfactory transfer makeup in the case of a transfer performed immediately after printing, or within 30 minutes thereof, but also in the case of a transfer performed a few days or even a few months after printing.

Finally, it may also be advantageous for the user to be able to retouch the transferred pattern within minutes of transferring, for example so as to be able to soften the contours and to smooth out the demarcations with the area not made up.

There is consequently a need for makeup devices that allow transfer makeup to be obtained by simple contact, without addition of solvent, whether the user seeks to transfer the pattern just after printing or after a longer or shorter period of storage of the device.

It would also be advantageous to obtain transfer makeup devices that allow the user, within minutes of transferring, to be able to retouch the pattern transferred onto the keratin materials, if necessary.

Moreover, the surface of the human body has substantially flat areas such as the back, surfaces that have a generally cylindrical shape (arms and legs) and also hollows and domed parts, in particular the area of the eyes, the lips, the nose, the armpits, the feet, etc.

Now, transfer using the known systems is generally performed via flat transfer surfaces, for example printable plastic sheets, which have difficulty in adapting to the curved parts of the body. There is consequently a need for a transfer makeup device adapted to the various parts of the body, especially those bearing reliefs. For these parts, it is important for the pattern to be applied faithfully, following the skin relief.

The present invention is directed towards meeting all or some of these needs.

SUMMARY

According to a first aspect, the present invention relates to a printer containing at least one cosmetic ink and designed to allow the formation of a coat of cosmetic ink on a non-flat transfer surface defined by a substrate and intended to transfer the coat of ink by contact onto human keratin materials.

The term "human keratin materials" denotes the skin, including the scalp, the lips, the nails, the hair, the eyelashes and the eyebrows; preferably the skin.

The term "digital printer" means a machine for printing in the form of pixels using digital data, different from a machine comprising a printing form.

The use of at least one coat of cosmetic ink obtained by printing using a digital printer advantageously makes it possible to obtain great precision for a complex and customizable makeup.

The invention advantageously makes it possible directly to print the coat of cosmetic ink onto a non-flat transfer surface, corresponding especially to the outer surface of a roller or pad, which facilitates the subsequent transfer onto areas of the body bearing reliefs. A roller is particularly advantageous for large areas, and pads are suitable for smaller areas.

By means of the invention, the transfer surface adapts easily to the relief of the area to be made up and makes it possible to obtain good transfer even on hollow or protruding areas of the body, in particular the area of the eyes, the lips, the nose, the armpits or the feet.

The printer may be an inkjet printer, for example a thermal or piezoelectric printer, a sublimation printer or a laser printer.

Preferentially, the printer comprises at least one cosmetic ink cartridge.

The printer may comprise several cartridges, especially several cartridges of different colours.

The term "ink" means a liquid or pulverulent ink, also referred to in the latter case as a toner.

When the colouring ink is liquid, it may have, for example, a viscosity ranging from 1 mPa·s to 500 mPa·s and preferably from 1 mPa·s to 300 mPa·s at 25° C.

The viscosity of an ink of the invention may be measured according to any process known to those skilled in the art, and especially according to the following conventional process. At 25° C. using a Rheomat 180 viscometer, equipped with a spindle rotating at 200 rpm, a person skilled in the art can select the spindle for measuring the viscosity from the spindles M1, M2, M3 and M4 on the basis of his general knowledge, so as to be able to perform the measurement.

The colouring ink may be in emulsion form.

In one example, the printer is a laser printer arranged to allow the formation by electrophotography or magnetophotography of a coat of ink having a pattern on a transfer surface using at least one cosmetic toner and to deliver the toner present on the transfer surface in a state that is sufficiently free to allow it to be taken up or transferred by contact with the human keratin materials.

The term "cosmetic toner" should be understood as meaning a pulverulent cosmetic composition that is compatible with the formation of an image via an electrophotographic or magnetophotographic process as used in laser printers. Preferably, it is a toner that is suitable for electrophotographic use.

The toner is cosmetic in the sense that it is compatible with an application to human keratin materials. Depending on the surface to be made up, the formulation of the toner may be different. For example, for an application to the hair or the nails, it is possible to use certain compounds that might not be used for an application to the lips, for example.

When the ink is in the form of a cosmetic toner, this toner may comprise, besides the colouring agent, a compound for controlling the electrical charge, a particular additional filler, a lubricant, a wax and/or a binder.

Preferably, the particles of the toner have a mean size of between 1 and 16 µm. The toner consists, for example, of pigments with a particle size of between 1 and 10 µm.

The transfer surface defines, for example, at least one cylinder or sphere portion.

The printer may advantageously comprise means for rotating a roller and/or a pad support, referred to hereinbelow as "roller drive means".

The roller drive means may comprise gears configured to synchronize the rotation of the roller with the sweeping of the printing nozzles.

The printer may comprise feet, especially adjustable feet, to avoid friction when the roller drive means rotate the roller or the pad(s) borne by the pad holder.

The printer may comprise a receptacle to house, at least at the time of printing, a roller or a pad holder bearing at least one pad.

The receptacle may make it possible to removably house the roller or the pad holder.

The receptacle may comprise at least one runner for inserting and removing the roller or the pad holder by guiding them. By means of the runners, once the roller or the pad holder has been inserted in the runners, the transfer surface comes close to the printing nozzles. The distance between the nozzles and the transfer surface is, for example, between 0.1 mm and 5 mm and preferably between 0.1 mm and 2 mm.

The printer may comprise a roller or a pad holder, which are, for example, removable, especially to facilitate the cleaning of the transfer surface and to make it possible to select the use of a pad holder or a roller from an available range.

In one variant, the printer comprises a window for access to the transfer surface and transfer of the ink is possible while the substrate is present in the printer.

The printing width is, for example, between 0.2 and 40 cm, preferably between 5 and 200 mm, especially between 10 and 120 mm, better still between 10 and 80 mm, or even between 10 and 60 mm.

Roller and Pad Holder

According to another aspect, the present invention relates to a roller intended to be used on a printer according to the invention, the roller bearing a deformable substrate defining the transfer surface, intended to receive an ink, especially a cosmetic ink, to be transferred by contact especially with the keratin materials, the transfer surface at least partly forming the outer surface of the roller.

The substrate may be fastened to the roller by any suitable means known to those skilled in the art, especially by friction or bonding.

In one variant, the roller comprises means for fastening the substrate, especially at least one fastening clip or jaw.

The roller may also comprise a removable substrate holder.

The substrate may embrace the reliefs of the roller, for example being moulded onto the roller. In one variant, there is a space between the substrate and the roller, especially at the time of printing. During the transfer, the substrate is plated against the roller and the transfer surface is deformed to coincide with the relief of the area to be made up.

The transfer surface is preferably domed.

The roller may have the form of a right cylinder. In one variant, the roller has the form of an irregular cylinder, for example the form of an hour glass.

In one variant, the roller is "premoulded", i.e. it has an initial non-flat form corresponding to the general form of the area to be made up, for example the negative of the lips, of an eye socket or of a forearm.

The space between the substrate and the roller, which extends especially between the face of the substrate opposite the transfer surface and the imprint, may be filled with a fluid, at least at the time of printing, for example compressed or non-compressed air, or a liquid.

A fluid is, for example, injected into the space between the imprint and the substrate to create an excess pressure during printing. The fluid is sucked up before the transfer to plate the substrate onto the roller.

The process may also comprise a step of finishing a pattern formed by at least one ink borne by the transfer surface. This pattern finishing step may be performed, for example, with the fingers or a special tool. For example, a pressure is applied to certain areas or certain areas are heated.

This step may be performed using a geometrical rectifications system as described later.

Once the ink has been transferred onto the keratin materials, the transfer surface is moved away from the area of the said materials and the substrate is then preferably removed from the roller.

The roller according to the invention may comprise a holding system, especially a handle to be housed removably in the printer at the time of printing. The holding system thus serves to hold the roller at least during its positioning for the printing and, in a preferred variant, also during the transfer.

The handle comprises, for example, two symmetrical jaws configured so as to be assembled at the two ends of a roller.

The handle may comprise a device for indexing and/or blocking the rotation of the roller.

Preferably, the holding system is removable. The holding system is in particular arranged so as to be able to be used with several rollers.

The roller may be heated.

The roller may be filled.

In one variant, the roller is hollow and in particular arranged to house a heating element.

According to yet another of its aspects, a subject of the present invention is a pad holder intended to be used with a printer according to the invention.

The pad holder is arranged to bear at least one pad bearing a substrate with a transfer surface, in particular intended to come into contact with the keratin materials.

The pad holder may bear a single pad.

The pad holder may be designed to hold several pads simultaneously, especially between 2 and 5 pads, for example 3 pads.

A pad may thus correspond to a cylinder part, for example defined by an angle of between 10° and 210°. The cylinder part is especially between $\frac{1}{10}$ and $\frac{4}{5}$ of a cylinder, in particular between $\frac{1}{5}$ and $\frac{3}{4}$ of a cylinder, or may even correspond to a quarter-cylinder or a half-cylinder.

In one variant, the substrate fastened to the pad is premoulded, for example for producing transfer makeup on an eyelid.

The pad holder may comprise a holding system, to be housed removably with the pad(s) in the printer at the time of printing.

The system for holding the pad holder is preferably removable. It may be identical to the holding system described above. In particular, it may be used, without preference, with a roller or with a pad holder according to the invention.

In one embodiment example, the substrate comprises an indication printed with the same ink or not with the same ink as that intended to be transferred. The indication states, for example, the nature of the keratin materials intended to be made up with the colouring ink or illustrates to scale, enlarged, reduced or otherwise and "right-side up" the pattern deposited "wrong-side up" on the substrate.

The process may also comprise the rectification of the pattern by a geometrical rectification system. Insofar as the surface is deformable, during the transfer onto the keratin materials, the pattern will be geometrically deformed (for example extension in one of the two dimensions). As a result, the pattern is printed with a geometrical deformation (in the present case reduction according to the deformable dimension(s)) such that, after application, the pattern is at the desired scale. Geometrical rules: either universal or specific, may be applied to the pattern to be printed on the transfer surface so that the pattern has the desired form after transfer onto the area of the keratin materials to be treated. Such a rectification system is particularly advantageous with a premoulded roller. In this case, use will be made in particular of specific geometrical rules adapted to the area to be treated and/or to the desired pattern.

Assemblies

According to another aspect, a subject of the invention is an assembly comprising several rollers according to the invention, the rollers differing by the thickness of the substrate and having the same diameter, measured when the substrate is in place on the roller, the diameter with substrate especially being between 0.5 and 20 cm or even between 1 and 10 cm.

According to another of its aspects, the present invention relates to a cosmetic assembly comprising, in the same packaging, a plurality of rollers and/or pads as defined above.

The assembly may comprise a pad holder and/or at least one pad.

A roller and/or a pad of the assembly may or may not comprise a colouring ink, deposited onto their transfer surface.

The rollers or pads may differ by the form and/or composition of the substrate, in particular the transfer surface intended to engage with the keratin materials.

The rollers or pads may differ by the chemical nature of the colouring ink that they bear and/or by the pattern thereby formed.

The assembly may comprise at least one ink cartridge.

The assembly may also comprise a printer according to the invention.

According to another aspect, a subject of the invention is a cartridge of cosmetic ink, characterized in that it comprises a case containing a cosmetic ink or toner, the case being designed to be received inside a printer according to the invention as described previously.

Printing

According to yet another aspect, the present invention relates to a process for manufacturing a transfer device for making up human keratin materials, comprising the step consisting in printing, onto a non-flat transfer surface intended to transfer the ink by contact with the human keratin materials, a coat of cosmetic ink using at least one printer according to the invention, as described previously.

In one embodiment example, the colouring ink is printed in a predefined pattern.

The process may comprise a step of choosing and/or making the pattern by a user and of transmitting, by means of a machine connected to the printer that performs the printing, information relating to this pattern.

The machine may be a computer, an advanced portable telephone, also known as a "smartphone", or a tablet computer. The machine may be connected physically and/or by means of a data exchange network to the said printer.

The colouring ink may be in liquid or pulverulent form when borne by the transfer surface and before application to the keratin materials.

In a particularly preferred manner, the ink is capable of transferring onto the keratin materials without addition of an intermediary fluid compound, especially a liquid. In other words, the colouring ink may transfer onto the keratin materials by simple contact of the area intended to be made up with the said colouring ink, without it being necessary to apply an intermediary liquid intended to improve the transfer of the ink, as in the case of decal transfers.

The colouring ink obtained by printing may be deposited in the form of spots and/or of raster lines, so as to form a halftone image, for example a monochromatic or polychromatic image.

The pattern formed by the colouring ink printed on the transfer surface may be of any type.

This pattern may reproduce the appearance of relief and/or colour heterogeneities of the skin, for example freckles or a mole.

The printing may also follow geometrical rectification rules. In so far as the transfer surface is deformable, during the application, the pattern may be geometrically deformed (for example extension in one of the two dimensions). As a result, the pattern is printed with a geometrical deformation (in the present case reduction according to the deformable dimension(s)) such that, after application, the pattern is at the desired scale. Geometrical rules: either universal or specific, may be applied to the pattern to be printed on the transfer surface so that the pattern has the desired form after transfer onto the area of the keratin materials to be treated. The use of such rectification rules is particularly advantageous with a substrate that has a transfer surface bearing reliefs, in particular in order to embrace the form of an imprint, as will be seen later. Use may be made in particular of specific geometrical rules adapted to the area to be treated and/or to the desired pattern.

The pattern formed by the colouring ink borne by the transfer surface may be coloured when observed under white light in the visible region (400 nm-800 nm). As a variant, the pattern is colourless under white light in the visible region, but may appear coloured when submitted to a chemical and/or energy stimulus, such as exposure to UV (365 nm-400 nm), for example when the colouring ink contains a photochromic or fluorescent dyestuff.

The printing may use several different inks, especially inks of different colours.

The printing may use at least three, especially at least four, five, six, seven, eight, nine, ten, eleven or twelve colouring inks of different colours.

The printing may use only colouring inks that produce primary colours. As a variant, the printing may use both inks that produce primary colours and at least one colouring ink that produces a non-primary colour.

The printing of the colouring ink may be three-colour or four-colour printing.

The pattern obtained by printing may comprise several areas of different colours. As a variant, the pattern obtained by printing is a flat tint.

The colouring ink may be deposited in several printing passes. In other words, a first fraction of the colouring ink may first be printed onto the transfer surface, followed by a second fraction of the colouring ink on all or part of the first fraction.

Substrate

The substrate is preferentially non-absorbent. The substrate is advantageously non-porous, at least on the transfer surface intended to receive the cosmetic ink.

The substrate comprises or consists of a deformable material, especially a thermoplastic and/or elastomeric material.

Preferably, the substrate is elastically deformable. The substrate may be single-layered or multi-layered.

The substrate is advantageously compressible. In order especially to increase its compressibility, the substrate may comprise one or more porous layers, especially at its core. The substrate may comprise a material incorporating alveolae or microspheres.

Preferably, the substrate is prepared such that, during the transfer of ink onto the keratin materials, the substrate is easily deformable by simple pressure exerted on the face opposite the transfer surface, which improves its contact with the keratin materials.

The transfer surface may be defined by all or part of: the outer surface of an applicator roller, the surface of an applicator pad, an element in sheet form, a patch, the surface of a porous foam, especially a sponge or a wipe.

The transfer surface may be defined by a mixture of elastomers.

The transfer surface is defined, for example, by at least one elastomer chosen from the following non-limiting list: copolymerized butadiene-styrene, butadiene-nitrile, isobutylene-isoprene, copolymerized chloroethylene-polysulfide, polysulfides, EPDM (ethylene-propylene-diene monomer) or polyethylene-propylene diamine or polyurethanes.

The substrate comprises, for example, an elastomer, especially a silicone elastomer, for example VMQ or MQ, FVMQ, PVMQ (described in the publication by R. B. Simpson 2002, Rubber Basics, p. 96-ISBN 1-85957-307-X). An example of an elastomer that may be used is the one sold under the name Patsil® GEL 10 by the company Polytek.

The material defining the transfer surface may comprise at least one additional filler, a plasticizer (for example glycol ethers, phthalates or silicone oils), a colouring agent (pigment or dye), a protective agent for increasing the resistance to light (UV-screening agents), a vulcanizing agent and/or a vulcanization accelerator (sulfur, zinc oxide).

The additional compound(s) present in the material defining the transfer surface may in particular serve to improve the resistance to the oils and solvents present in the ink or used for cleaning the substrate.

The transfer surface may be brought into its final form by moulding (especially for crosslinkable materials), machining, laser machining, sintering, sanding, calendering a substrate, etc.

The transfer surface is preferably smooth and has a roughness of less than or equal to 1 mm and especially between 1 and 100 μm. The roughness is measured using a roughness meter, the tip of which has a radius of curvature of 10 mm, and the force of which, applied to the material to be characterized, is 6 mN.

The substrate may have a hardness of between 1 and 30 Shore A, for example equal to 10 Shore A, measured according to standard DIN 53 505, ISO/R868.

The thickness of the substrate may be adapted to the keratin materials to be made up.

The thickness of the substrate corresponds to its dimension measured perpendicular to the transfer surface. Depending on the position on the transfer surface, the thickness of the substrate may or may not be constant.

For example, when the colouring ink is intended to be applied to the cheeks and/or the nails, the substrate may have a thickness of between 1 mm and 3 mm, or even more than 3 mm.

In one embodiment example, the colouring ink is intended to be applied to the area around the eyes and/or to the lips, and the substrate has a thickness of between 3 mm and 1 cm, or even more than 1 cm.

In another embodiment example, the colouring ink is intended to be applied to the nose and/or in the area of the ears, and the substrate has a greater thickness, between 1 cm and 3 cm, or even more than 3 cm.

In one variant, the substrate and/or the support especially in roller form is made in a "premoulded" form so as to facilitate its adaptation to the relief of the keratin materials, for example the negative of the lips or of the eye socket.

The substrate may be in the form of a printer's blanket, especially as used in the printing sector, comprising, in a known manner, a carcass for ensuring the mechanical performance qualities and a blanket layer, also known as a top, defining the transfer surface, and whose job is to provide the transfer performance qualities.

In one embodiment example, the substrate is at least partly covered with a coating, which may be coloured and which is itself capable of transferring onto the human keratin materials. The coating may be coloured a colour that is difficult to print, for example white or black, or a colour close to the flesh tone of the skin to be made up, such as a flesh colour. As a variant, the coating is not itself coloured.

The coating may comprise adjuvants for improving the transfer, such as oily substances, and/or for improving the persistence and/or for protecting the skin, such as sunscreens.

This or these coatings may also be applied to the substrate after it has been printed with the colouring ink.

In one embodiment example, the substrate comprises at least one translucent or transparent area.

The translucent or transparent area allows a user to see through the substrate and thus to visualize more easily the surface to be made up before transferring the colouring ink. The presence of a translucent or transparent area thus advantageously contributes towards facilitating the production of a precise makeup result.

The translucent or transparent area can be totally or partly superposed with the layer of colouring ink, and especially may overlap with it.

The layer of colouring ink may be superposed in its entirety on the translucent or transparent area. As a variant, only part of the layer of colouring ink is superposed on the transparent area.

The substrate may be made entirely of a transparent or translucent material. In this case, the translucent or transparent area extends over the entire surface of the substrate.

According to another aspect, a subject of the invention is a process for making up an area of human keratin materials using a makeup device according to the invention, comprising a substrate bearing a non-flat transfer surface intended to come into contact with the keratin materials and configured to receive a cosmetic ink.

The process may comprise the following steps:
printing, using at least one printer according to the invention, a coat of cosmetic ink onto the transfer surface,
placing the coat of ink in contact with the area to be made up.

The substrate may be fastened to the printer during the transfer of the coat of ink onto the area to be made up, for example when the transfer surface is defined by the outer surface of a roller. The user may use the body of the printer as a gripping means.

DESCRIPTION OF THE FIGURES

The invention may be understood more clearly on reading the following description of non-limiting implementation examples thereof, and on examining the attached drawing, in which.

Figures 1A, 1B, 1C, 2A, 2B:
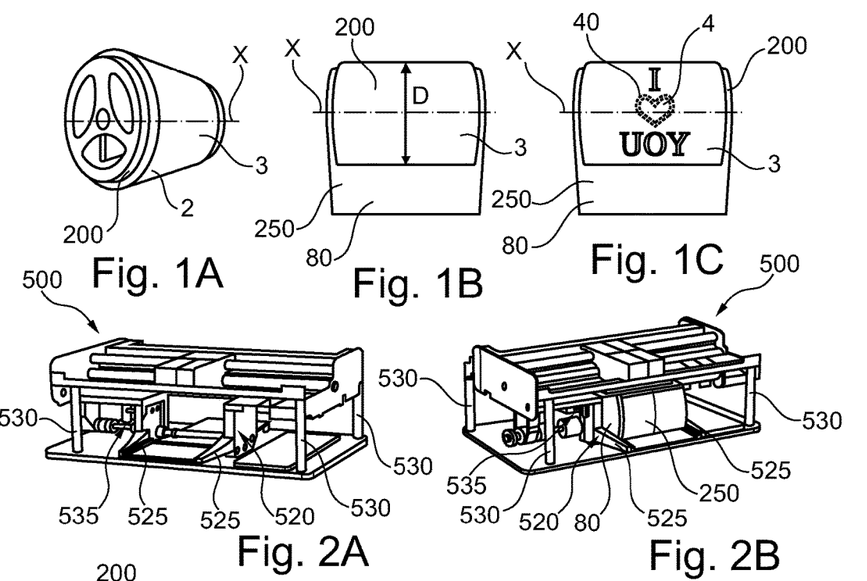
FIGS. 1A-1C represent, in perspective and in elevation, an example of a roller according to the invention.
FIGS. 2A and 2B represent the roller of FIGS. 1A-1C and a printer according to the invention.

FIG. 1A shows a roller 200 according to the invention, comprising a substrate 2 defining a transfer surface 3.

The substrate 2 is made of a flexible, compressible and deformable material.

The substrate 2 consists in the illustrated example of a printing blanket made of elastomeric material, plated onto the hollow roller 200 to which it is fastened by simple friction.

The transfer surface 3 is smooth and has a roughness of less than or equal to 50 µm measured using a roughness meter as described above.

The transfer surface 3 is intended to receive a coat of cosmetic colouring ink 4, to produce a transfer makeup result.

To deposit the coat of colouring ink 4 onto the transfer surface 3, use is made of a digital printer 500 shown in FIGS. 2A and 2B, which deposits the ink dots in correspondence with the pixels of an image to be reproduced.

As illustrated in FIG. 1B, a removable handle 80 may be made integral with the roller 200 to serve as a handling member during the transfer of the ink.

It is advantageous for the handling member 80 to be removable; thus, it may be removed as illustrated in FIG. 1A to allow the substrate 2 to be plated more easily onto the roller 200 and to allow cleaning between two uses. The handle 80 comprises, in the example, two plastic jaws made of POM produced by machining, which are intended to be assembled to the two ends of the roller 200.

In the example under consideration, the handling member constitutes the means 250 for holding the roller 200 in the printer used during printing.

As a variant, the holding system is different.

The receptacle may make it possible to removably house the roller or the pad holder assembled to the holding system 250, in particular in the form of a handle 80.

The receptacle may comprise at least one runner for inserting and removing the roller or the pad holder by guiding them. By means of the runners, once the roller or the pad holder has been inserted in the runners, the transfer surface comes close to the printing nozzles. The distance between the nozzles and the transfer surface is, for example, between 0.1 mm and 5 mm and especially between 0.1 mm and 2 mm.

During printing, the roller 1 is assembled with the printer 500 by means of the cooperation of a holding system 250 of the device 1 with a second holding system 520 of the printer 500, allowing, for example, click-fastening of the applicator roller onto the printer 500.

In FIGS. 2A and 2B, the outer case of the printer 500 has been removed in order to illustrate the integration of a device according to the invention, for example comprising a roller as illustrated or a pad holder.

The printer 500 comprises a receptacle 520 to house, at least at the time of printing, a roller 200 or a pad holder 350 bearing at least one pad 300.

Whereas FIG. 2A shows the receptacle 520 in the absence of a roller and a pad holder, FIG. 2B shows the printer 500 housing the handle 80 assembled with the roller 200 of FIGS. 1A to 1C. The roller is not visible in the figure.

In one variant, a pad holder bearing, for example, three pads has been assembled with the handle 80.

The receptacle 520 comprises, for example, two runners 525 for receiving and guiding the handle 80 assembled with the roller or with the pad holder and thus for facilitating their insertion in and their removal from the receptacle 520. The transfer surface 3 is thus placed close to the printing nozzles to allow good precision of the pattern formed by the coat of ink 4. The distance between the nozzles and the transfer surface is, for example, between 0.5 mm and 1.5 mm.

The printer 500 also comprises roller drive means 535 comprising gears configured to make the substrate 2 pass through at the time of printing and to synchronize the rotation of the roller 200 with the sweeping of the printing nozzles.

The roller drive means 525 are, for example, at least partly located in a flange to the left of the receptacle 520.

The printer also comprises four feet 530, for example adjustable feet, for preventing, during the printing, friction of the roller or of the pad(s) borne by the pad holder and driven in rotation.

FIG. 1C represents the device 1 once removed from the printer 500, the transfer surface 3 bearing a coat of cosmetic ink 4.

A pattern 40 representing in inverted form the image to be produced is printed directly onto the transfer surface 3 using the printer 500.

The coat of ink 4 may form any type of pattern. The pattern may consist of several inks.

The substrate 2 may bear an indication 7, for example formed by printing, for providing information regarding a recommended positioning for the makeup, or providing information regarding the nature of the keratin materials intended to be made up with the ink 4, or the like.

The roller 200 may also comprise a heating member, not shown, for example located inside the roller.

Figure 3:
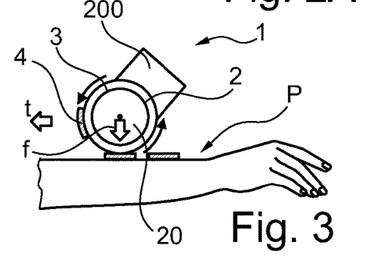
FIG. 3 illustrates a makeup process according to the invention, using the roller of FIGS. 1A-1C, FIGS. 4 and 5 represent examples of cosmetic assemblies according to the invention.

FIG. 3 schematically shows an example of a makeup process according to the invention.

The roller 200 of FIGS. 1A-C, once the printing has been performed, is, for example, taken out of the receptacle 520.

The transfer makeup may be performed just after printing or within 30 minutes thereof, but also within a few days, or even a few months after printing.

By holding the handle 80, the user brings the roller 200 towards the keratin materials so as to place in contact, as illustrated, the coat of colouring ink 4 with the area P to be made up, the forearm in the illustrated example.

The area P is preferably dry. The user then rolls the transfer surface 3 while applying a pressure to transfer the colouring ink 4 onto the area P to be made up. As illustrated by the arrow f, the pressure is applied by means of the roller 200 on the face of the substrate opposite the transfer surface 3.

During contact with the keratin materials, the roller 200 advances in the direction of the arrow t and the substrate 2 is preferably not moved sideways so as not to affect the appearance of the transferred pattern.

The pattern transferred onto the keratin materials corresponds in positive to the pattern 40 formed in negative by the coat of colouring ink 4 when it is present on the substrate 2

(i.e. when it has not yet been transferred onto the keratin materials to be made up) and faithfully reproduces the starting image.

In one variant, not shown, the printer is sufficiently small and easy to manoeuvre to bring it directly up to the keratin fibres and to perform the transfer without removing the roller.

Figure 4:
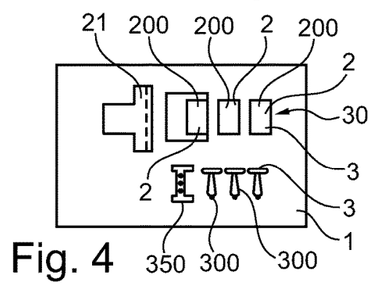

FIG. 4 shows an embodiment variant of a cosmetic assembly 30 according to the invention, which comprises a plurality of rollers 200 and a pad holder 350 according to the invention. A first roller 200 is, for example, assembled with a handle 80 which may serve as a system 250 for holding on a printer as seen above.

The cosmetic assembly 30 comprises several rollers 200 arranged to bear substrates 2 of different thicknesses. All the rollers 200 of the assembly have the same diameter D, measured with the substrate fastened to the roller. Each diameter d of empty roller 200, i.e. before fastening the substrate, corresponds to a thickness e of substrate such that the transfer surface of the device defines a cylinder of diameter D, in particular 60 mm in diameter.

Figure 8:
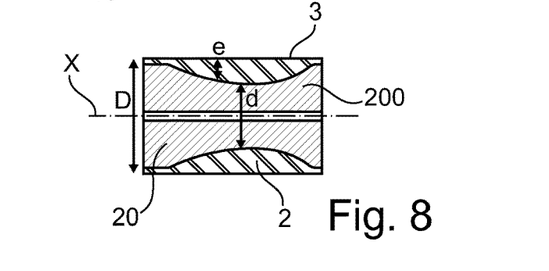
FIG. 8 is a partial view in cross section of a variant of a roller according to the invention.

As illustrated in FIG. 8, the thickness e and the diameter d may vary along the longitudinal axis of the roller.

Each roller 200 comprises a substrate 2 with a transfer surface 3 intended to be printed with the colouring ink, the substrate 2 especially being plated onto the roller.

Holding System

The cosmetic assembly 30 also comprises a pad holder 350 that can be adapted to the handle 80 and also several pads 300 and a strip of elastomeric film to be cut and bonded as substrate onto the pads.

The devices do not comprise any coat of ink and the cosmetic assembly 10 comprises, for example, in the same packaging, a printer cartridge 21 comprising one or more cosmetic colouring inks intended to be deposited onto the transfer surfaces 3. In one variant, not shown, the assembly comprises several cartridges, containing, for example, different inks.

This cosmetic assembly may be provided to the user, where appropriate, with the printer intended to use the cartridge.

Figure 5:
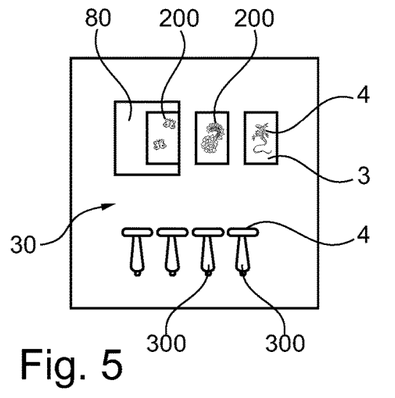

In another example, illustrated in FIG. 5, each of the rollers 200 or of the pads 300 comprises on its transfer surface 3 a coat of colouring ink 4 forming a pattern 40 that is inverted relative to the desired pattern. The packaging is then preferably leaktight so as to prevent the inks from drying out. The packaging may be made with means for avoiding contact of the inks with a surface other than the transfer surface, so as to reduce the risk of premature transfer. For example, the packaging comprises a thermoformed shell whose wall extends a distance from the transfer surfaces covered with inks.

Figure 9:
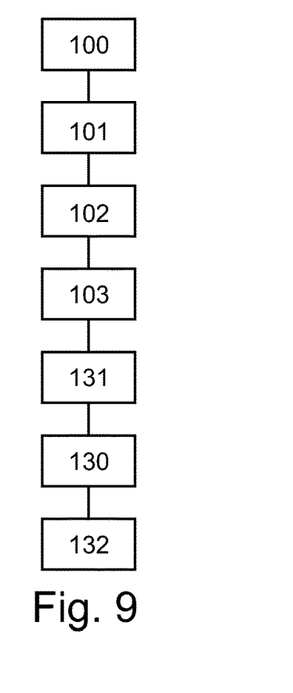
FIG. 9 is a block diagram illustrating the various steps of a makeup process according to the invention.

An example of a makeup process according to the invention will now be described, with reference to FIG. 9.

The process comprises the printing of a pattern to be transferred, and may also comprise steps 100 to 103 of choosing the pattern.

In a first step 100, various patterns are proposed to the user, for example by displaying on the screen of a machine.

The range of patterns proposed may correspond to several areas of makeup requiring several different transfer devices.

Step 101 of choosing the pattern by the user may comprise an action such as pressing on a touchscreen in order to select the pattern intended to be printed.

The machine may also provide the user with a simulation of the makeup result. Thus, the machine may display a simulation of the appearance of the keratin materials made up with the chosen or produced pattern. To do this, the machine may acquire at least one image of the keratin materials to be made up.

In one variant, the user makes a computer file with the pattern that he wishes to print. In this case, the user may use drawing software for making such a pattern, and edit it, for example, in a file in .jpg image format.

Once the pattern has been chosen or made, in step 102, the machine sends to the printer the data necessary for printing the pattern, and in particular specifies the device to be used. This device may be selected from a range of devices suited to the area to be made up and to the chosen pattern, for example in the form of rollers 200 or pads 300, during step 111.

The device, for example a roller or pad fastened to a pad holder, is then, in step 103, assembled to the printer by means of a holding system 250, for example a handle 80.

The machine may be connected physically and/or by means of a network to the printer performing the printing.

Once the data have been received and the device has been placed in a receptacle 520 of the printer, in step 103, a coat of ink 4 with the inverted pattern is printed on the transfer surface 3. FIG. 1C illustrates patterns thus printed onto the transfer surface of a roller 200 according to the invention.

The printer driver may comprise a menu for selecting a cosmetic ink cartridge among other cartridges installed in the printer and/or the nature of the substrate that is printed. As a variant, the printer automatically recognizes that the cartridge installed is a cosmetic ink and adjusts the operating parameters in consequence. The cartridge may thus comprise an identifier, for example an electronic chip, for providing the printer with information relating to the nature of the colouring ink that it contains, especially that this ink is of cosmetic nature.

In one embodiment example, the printer is configured to prohibit printing if the assembled device does not correspond to the chosen pattern and/or if the presence of a cartridge comprising a composition not intended to be placed in contact with human keratin materials, especially the skin, the nails or the lips, is detected.

As a variant, the printer may perform printing even if the presence of a cartridge comprising a composition not intended to be placed in contact with human keratin materials, especially the skin, the nails or the lips, is detected, this non-cosmetic ink cartridge possibly being used for printing on the substrate an indication 7 relating to the cosmetic colouring ink borne by the transfer surface and/or the nature of the keratin materials to be made up.

The printing of the substrate may take place in several passes, to make successive deposits of ink at the same place, so as to increase the amount of ink deposited on the substrate. The substrate may effect, for example, between 1 and 20 passes in the printer and the amount of cosmetic ink dry matter deposited ranges, for example, from 0.1 mg/cm$^2$ to 10 mg/cm$^2$ and better still from 0.2 mg/cm$^2$ to 5 mg/cm$^2$.

The pattern may be monochromatic or, better still, polychromatic. In this case, printing may be performed at each passage in the printer with several cosmetic inks that are locally juxtaposed at the microscopic scale, depending on the colour to be reproduced.

The printing resolution may be between 16 dpi and 2048 dpi.

In a manner known to those skilled in the art, the printer may be arranged to detect if the ink previously deposited on the substrate is sufficiently dry before printing a new coat of ink.

The printer and/or the printer driver may be made so as to inform the user of the need to wait a predefined time before performing a new printing on the already-printed substrate. The printer and/or the driver may automatically suspend the printing of an already-printed substrate if sufficient time has not passed to allow sufficient drying. The printer is preferably arranged so as not to deliver the printed substrate as long as all the coats of ink to be printed have not been printed.

The device is then optionally separated from the printer in order for the ink to be able to be transferred onto the keratin materials.

Transfer then takes place during step 130 by simple contact of the transfer surface 3 with the keratin materials P, especially by rolling the device on the keratin materials in the case of a device in the form of a roller 200 as illustrated in FIG. 3, or application of the imprint 60 covered with the substrate 2 as in FIGS. 5D and 5E. The transfer is facilitated by pressing the device against the keratin materials during step 130.

Step 130 may be preceded by a step 131 of finishing the pattern on the transfer surface. This step of finishing the pattern deposited on the transfer surface may be performed with the fingers and/or a special tool. For example, a pressure is applied to certain regions or certain regions are heated.

Step 130 may be followed by a step 132 of finishing the makeup application.

Step 130 may comprise heating of the device.

Figure 7A:
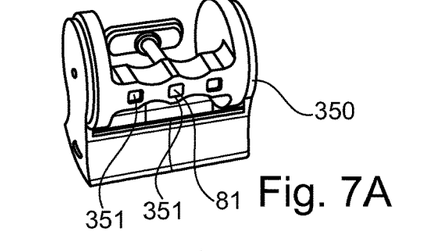
FIGS. 7A to 7D show in elevation a pad holder according to the invention.

FIG. 7A shows a roller variant 200 according to the invention before fastening the substrate 2. The roller 200 may be assembled to a handle 80 similar to the handle of the system in FIGS. 1A to 1C. This handle 80 may be used with several different rollers 200, adapted to different thicknesses of substrate and different modes of fastening.

Whereas the substrate in the embodiment example of FIGS. 1A to 1C was fastened by friction to the support, a roller according to the invention may comprise a means 25 for fastening a substrate 2.

Figure 6A:
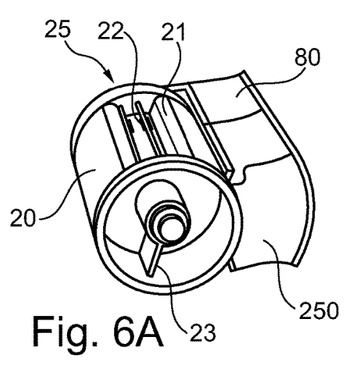
FIGS. 6A to 6C show in elevation other examples of a roller according to the invention before fastening the substrate.

The fastening means 25 illustrated in FIG. 6A comprise a groove 21 on the outer surface of the roller, a double clip 22 whose opening is driven by cams located at each end of the roller 200 and a system of springs, not shown, for keeping the double clip closed.

Figure 6B:
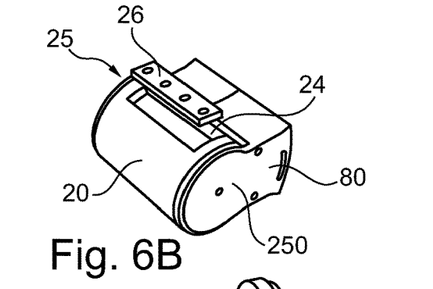

In the example illustrated in FIG. 6B, the means 25 for fastening the substrate to the roller comprise a fastening jaw 26 arranged to be fastened, for example by screwing, in a housing 24 of the roller, holding the substrate in position.

The empty diameter d of the roller 200 is chosen so as to correspond to the thickness e of the substrate such that, once the substrate 2 is in position, the transfer surface 3 forms a cylinder of diameter D, for example 60 mm.

FIGS. 7A to 7D illustrate a pad holder 350 according to the invention, intended to be assembled with a holding system 250, in particular with the handle 80, for example a pad holder 350 which may simultaneously receive three pads.

A substrate 2 is bonded to the outer surface of each pad 300; the substrates 2 are, for example, cut out of an elastomeric film bonded to the support.

In another variant, a pad holder 350 according to the invention may receive, for example, between two and four pads, or even five pads.

Preferentially, the pad holder 350 and the pads 300 are configured so that the transfer surfaces of the pads belong to a cylindrical envelope surface, in particular 60 mm in diameter.

Figure 7B:
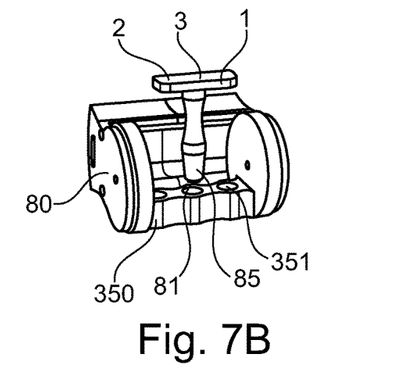

In FIG. 7A, the pad holder 350 bears only one pad 300. FIG. 7B shows the same pad 300 off the pad holder 350. The pad 300 comprises a sleeve 85 for fastening it in a housing 351 of the pad holder 350. The sleeve 85 ends with a square end piece 81 which prevents its rotation in the housing 351.

The pads may correspond to a cylinder part, for example defined by an angle of between 10° and 210°. The cylinder part is especially between ¹⁄₁₀ and ⅘ of a cylinder, in particular between ⅕ and ¾ of a cylinder, or may even correspond to a quarter-cylinder or a half-cylinder. Thus, the pad 300 illustrated in FIGS. 7A and 7B has a transfer surface 3 of oblong and cylindrical form along its large axis, corresponding to an angle α of 10°.

Figure 7C:
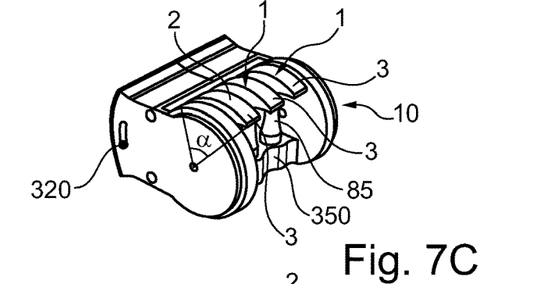

FIG. 7C shows three pads 300 whose transfer surface is a cylinder portion defining a quarter-cylinder.

The pads of FIG. 7C are of oblong and cylindrical form along their small axis.

Figure 7D:
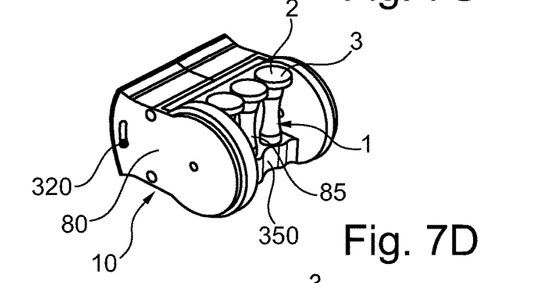

The device variant of FIG. 7D comprises three pads of spherical form.

In one variant, not shown, the outer surfaces of the pads 300 are flat.

In another example not shown, the substrate fastened to the pad is premoulded.

The handle 80 may comprise, as shown in FIG. 7C, a device 320 for indexing and blocking the rotation of the roller 200 or of the pad holder 350.

EXAMPLES

The examples correspond to the embodiment with a roller.

Four inks corresponding to the formulations given in the table below were prepared:

These compositions are introduced into Canon printer cartridges.

TABLE 1

|  | Yellow I | Magenta I | Cyan I | Black I |
| --- | --- | --- | --- | --- |
| Dye | D&C Yellow 8 1% | FD&C Red 4 1% | FD&C Blue 1 1% | (1) 1% |
| Ethylene glycol |  | 4% | 6% | 5% |
| Diethylene glycol | 8% |  |  |  |
| 1,5-Pentanediol |  | 4% | 4% |  |
| 2-Pyrrolidone | 5% | 5% | 4% |  |
| Glycerol | 8% | 3% | 4% | 7% |
| 2-Imidazolidinone | 4% | 4% | 4% | 9% |
| Water | 76% | 79% | 77% | 78% |
| Total | 100% | 100% | 100% | 100% |

(1) Brown-Replacement-J from Sensient

A Canon Pixma IP100 printer was used, the case of which was removed. The sheet entertainment system found therein was replaced with roller drive means, while leaving the gears. The roller drive means are configured to be adapted to the gears of the printer. They make it possible to drive a roller and especially a roller or a pad holder according to the invention. A runner system was installed in the printer body so as to insert and remove the roller assembled with a handle. The sheet presence system was modified so as not to prevent the printer from functioning.

Several rollers were prepared.

Example 1

In this first version, the roller is filled and cylindrical with a diameter of 60 mm and a length of 80 mm. It is made of hard plastic of Delrin® type (from Dupont) and is covered with a film of thickness e equal to 2 mm made of Plat-Sil gel 10' silicone elastomer from the company Mouldlife, forming a substrate 2.

This roller is particularly suited to relatively flat large surfaces such as the back.

Figure 6C:
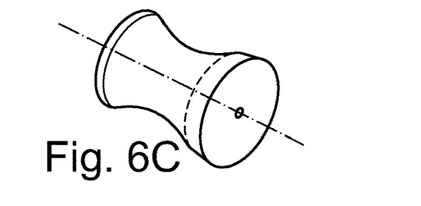

Example 2) FIGS. 6C and 8

In this example, the roller is filled and in the form of an hour glass. The empty diameter d at the centre is 20 mm smaller than at the ends.

A Plat-Sil gel 10' elastomeric silicone coating from the company Mouldlife is moulded around this roller so as to give the roller a cylindrical form with a diameter D equal to 60 mm.

The central part of the substrate is softer than the side parts, which makes this type of roller particularly suited to domed body areas such as the chin or the arms.

Example 3) For Transfer Makeup Application to the Arms

An alginate composition (Alginate for moulding from Esprit composite) is applied to an arm over a length of 20 cm and a width of 8 cm.

After setting solid, the imprint that has just been made is rolled up so as to make the two ends touch. A flexible object in the form of an hour glass is thereby obtained.

A mould is made from this object in two parts.

The two parts of the mould are opened to remove therefrom the flexible object made with the imprint.

A polymerizable resin composition is then introduced into the two parts of the mould, via a hole made therein.

After curing, the cast is removed from the mould. The process is then performed as in the preceding example by applying a Plat-Sil gel 10' flexible elastomeric composition from the company Mouldlife so as to make a cylinder.

This roller is especially suitable for printing on the arm.

The invention claimed is:

1. A printer containing at least one cosmetic ink and designed to allow the formation of a coat of cosmetic ink on a non-flat transfer surface defined by a substrate and intended to transfer the coat of ink by contact onto human keratin materials,
   the printer comprising a roller,
   the roller comprising a holding system, so as to removably housed in the printer at the time of printing.

2. The printer according to claim 1, the transfer surface defining at least one cylinder or sphere portion.

3. The printer according to claim 1, comprising a means for rotating a roller and/or a pad holder, the transfer surface corresponding at least partly to an outer surface of the roller or, respectively, of a pad borne by the pad holder.

4. The printer according to claim 1, comprising a receptacle for removably housing a roller or a pad holder, the transfer surface corresponding at least partly to an outer surface of the roller or, respectively, of a pad borne by the pad holder.

5. The printer according to claim 1, comprising a window for access to the transfer surface allowing the transfer of the ink while the substrate is present in the printer.

6. The printer according to claim 1, the printer having a printing width being between 0.2 and 40 cm.

7. The printer according to claim 1, comprising several cartridges of cosmetic ink.

8. A roller for use on a printer according to claim 1, the roller bearing a deformable substrate defining the transfer surface intended to receive an ink, the transfer surface at least partly forming the outer surface of the roller.

9. The roller according to claim 8, the substrate being fastened to the roller by friction or bonding or by fastening means.

10. The roller according to claim 8, the roller being hollow.

11. A pad holder for use on a printer according to claim 1, designed to bear at least one pad bearing the substrate.

12. An assembly comprising several rollers according to claim 8, the rollers differing by the thickness of the substrate and having the same diameter, measured when the substrate is in place on the roller.

13. A cartridge of cosmetic ink, comprising a case containing a cosmetic ink or toner, the case being designed to be received inside a printer as defined in claim 1.

14. A process for manufacturing a transfer device for making up human keratin materials, comprising the step consisting in printing, onto a non-flat transfer surface intended to transfer the ink by contact with the human keratin materials, a coat of cosmetic ink using a printer according to claim 1.

15. The process for manufacturing a makeup device according to claim 14, the process comprising a step of choosing and/or making a pattern by a user and of transmitting, by means of a machine connected to a printer, information relating to this pattern.

16. A process for making up an area of human keratin materials using a makeup device comprising a substrate having a non-flat transfer surface intended to come into contact with the keratin materials and configured to receive a cosmetic ink,
   the process comprising the following steps:
      printing, using at least one printer according to claim 1, a coat of cosmetic ink onto the transfer surface,
      placing the coat of ink in contact with the area to be made up.

17. The process according to claim 16, the substrate being fastened to the printer during the transfer of the coat of ink onto the area.

\* \* \* \* \*